US00PP27754P3

(12) United States Plant Patent
Bolinder

(10) Patent No.: US PP27,754 P3
(45) Date of Patent: Mar. 7, 2017

(54) ***CLEMATIS* PLANT NAMED 'KBK06'**

(50) Latin Name: ***Clematis* hybrid**
Varietal Denomination: KBK06

(71) Applicant: Kjell Bolinder, Hoganas (SE)

(72) Inventor: Kjell Bolinder, Hoganas (SE)

( * ) Notice: Subject to any disclaimer, the term of this patent is extended or adjusted under 35 U.S.C. 154(b) by 63 days.

(21) Appl. No.: 14/545,363

(22) Filed: Apr. 27, 2015

(65) Prior Publication Data

US 2016/0316602 P1 Oct. 27, 2016

(51) Int. Cl.
*A01H 5/02* (2006.01)

(52) U.S. Cl.
USPC ..... Plt./228

(58) Field of Classification Search
USPC ..... Plt./228
See application file for complete search history.

*Primary Examiner* — Keith Robinson
(74) *Attorney, Agent, or Firm* — Cassandra Bright

(57) ABSTRACT

A new and distinct *Clematis* hybrid named 'KBK06' is disclosed, characterized by a distinctive violet-pink flowers, and dense, shrubby plant form. Plant habit is well suited for container plantings. Flowers in Spring (May/June), through Fall August/September. The new cultivar is a *Clematis* typically suited for ornamental container and landscape use.

1 Drawing Sheet

Latin name of the genus and species: *Clematis* hybrid.
Variety denomination: 'KBK06'.

BACKGROUND OF THE INVENTION

The new cultivar is the result of a planned breeding program in Hoganas Sweden. The inventor is Kjell Bolinder, a citizen of Sweden. The new variety was derived from an open-pollination. The seed parent, *Clematis* hybrid 'Vino' U.S. Plant Pat. No. 9,290 was grown in a situation allowing for pollination by several unidentified pollen parents. The new variety was discovered in June 2005.

After selecting and isolating the new cultivar, asexual reproduction of the new cultivar 'KBK06' was first performed in in Sweden, at a hobbyist nursery by vegetative cuttings in June 2006. 'KBK06' has since produced multiple generations, and has shown that the unique features of this cultivar are stable and reproduced true to type.

SUMMARY OF THE INVENTION

The cultivar 'KBK06' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KBK06'. These characteristics in combination distinguish 'KBK06' as a new and distinct *Clematis* cultivar:

1. Intense violet-pink flower color.
2. Stamens are white and silvery-grey.
3. Single flowers
4. Dense, bushy plant habit.
5. Suitability for container culture.
6. Short plants

PARENTAL COMPARISON

The new variety is similar to the seed parent in most horticultural characteristics, however plant of the new variety differ in the following:

1. Flower color of the new variety is deeper, more intense and with more purple tone.
2. Plants of the new variety are shorter and denser.

3. Flowers of the new variety are single, whereas flowers of 'Vino' are semi-double.

COMMERCIAL COMPARISON

Plants of the new cultivar 'KBK06' are similar to the commercial variety *Clematis* hybrid 'Beauty of Worcester' unpatented, in most horticultural characteristics. However, the new variety differs from 'Beauty of Worcester' in the following:

1. The new variety has larger flowers.
2. The new variety has a more violet-pink color, compared to the purple color of this comparator.
3. The new variety is denser and shrubbier than 'Beauty of Worcester'.
4. Flowers of the new variety are single, whereas flowers of 'Beauty of Worcester' are semi-double.

The new variety can also be compared to *Clematis* 'Lasurstern', unpatented, differing in the following characteristics:

1. The new variety has smaller flowers.
2. The new variety has a more violet-pink color, compared to the purple color of this comparator.
3. The new variety is denser and shrubbier than 'Lasurstern'.

BRIEF DESCRIPTION OF THE PHOTOGRAPH

The accompanying photograph in FIG. 1 illustrates in full color a typical mature flowers and foliage of 'KBK06' grown outdoors in Germany. The plant is approximately 8 months old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'KBK06' plants grown outdoors in Germany. The growing temperature ranged from 0° C. to 25° C. at night to 0° C. to 30° C. during the day. No artificial light, photoperiodic treatments or chemical treatments were given to the plants. Plants were pinched once. Measurements and numerical values represent averages of typical flowering types.

Botanical classification: *Clematis* hybrid 'KBK06'.

Age of the plant described: Approximately 8 months.

Container size of the plant described: Growing in the ground.

PROPAGATION

Typical method: Vegetative cuttings.

Time to initiate root developments: 21 days in the summer at 22° to 25° C.

Time to produce a rooted cutting/young plant: 40-50 days in the summer at 20° to 26° C.

Root description: Fine, fibrous.

PLANT

Growth habit: Shrubby climbing vine.

Time to produce a finished flowering plant: Approximately 12 months from an unrooted cutting to a deliverable plant, in a 1.5 or 2 liter size container.

Height: Approximately 150 to 240 cm, measured from the soil after approximately 8 months.

Plant spread: Approximately 60 cm.

Growth rate: Approximately 20 to 30 cm per month during the growing season on the Spring.

Branching characteristics: One main stem, easily making side branches from a pinch.

Length of main stem: Approximately 170 to 250 cm.

Diameter of main stem: Approximately 0.2 cm.

Main stem color: Near RHS Green 138B, heavily flushed Greyed-Purple 183B.

Main stem texture: Glabrous.

Internode length: Varies from 6.0 to 10.0 cm.

Strength: Strong, flexible, semi-woody.

FOLIAGE

Leaf:

- *Arrangement*.—Opposite, single.
- *Average length*.—Approximately 6 to 10 cm.
- *Average width*.—Approximately 3 to 5 cm.
- *Shape of blade*.—Oblong.
- *Apex*.—Acute.
- *Base*.—Cordate.
- *Attachment*.—Stalked.
- *Margin*.—Entire.
- *Texture of both surfaces*.—Slightly bullate.
- *Color*.—Young foliage upper side: Near RHS Green 137A. Young foliage under side: Near RHS Green 138B. Mature foliage upper side: Near RHS Green 137A. Mature foliage under side: Near RHS Green 137C.
- *Venation*.—Type: Pinnate. Venation color upper side: Near RHS Yellow-Green 145C. Venation color under side: Near RHS Yellow-Green 145B.

Petiole:

- *Length*.—Approximately 5.0 to 7.0 cm.
- *Diameter*.—Approximately 0.2 cm.
- *Texture*.—Smooth.
- *Color*.—Near RHS Greyed-Red 181C.

FLOWER

Bloom period:

- *Natural season*.—May through June, and again August through September.
- *Inflorescence type and habit*.—Axillary, solitary, rotate. Flowers facing outward and slightly upward. Flowering occurring on both previous year's growth and current year's growth.

Rate of flower opening: Approximately 10 days from bud to fully opened flower.

Flower longevity on plant: Approximately 10 to 12 days, after fully opened. Self-cleaning.

Inflorescence size:

- *Diameter*.—Approximately 10 to 14 cm.
- *Depth*.—Approximately 3.0 cm.

Single flowers:

- *Corolla*.—Tepal arrangement: slightly overlapping single whorl. Quantity: Typically 6 to 8 per flower. Size: Length: Approximately 5.0 to 6.0 cm. Width: Approximately.1.0 to 1.5 cm. Margin: Slightly curved. Apex: Acute. Base: Blunt. Texture: Smooth.
- *Color*.—Tepals: When opening: Upper surface: Near RHS Red-Purple 71A. Lower surface: Near RHS Red-Purple 71D, center streak near Green-White 157A.
- *Fully opened*.—Upper surface: Near RHS Red-Purple 72A, over-hue near Purple 77A. Lower surface: Near RHS Red-Purple 72B, center streak near Purple 77C and 77D.
- *Ageing*.—Upper surface: Near RHS Red-Purple 72A, over-hue near Purple 77A. Lower surface: Near RHS Red-Purple 72B, center streak near Purple 77C and 77D.

Bud:

- *Shape*.—Conical.
- *Length*.—Approximately 2.7 cm.
- *Diameter*.—Approximately 1.9 cm.
- *Color*.—Near RHS Red-Purple 71D, heavily streaked Green-White 157A.

Peduncles:

- *Length*.—Average range 8 to 10 cm.
- *Width*.—Approximately 0.3 cm.
- *Angle*.—Average 75°.
- *Strength*.—Flexible.
- *Color*.—Near RHS Green 138A heavily flushed Greyed-Purple N186C.

Fragrance: None.

REPRODUCTIVE ORGANS

Stamens:

- *Number*.—Average 60 to 70 per flower.
- *Stamen length*.—Approximately 3.2 cm.
- *Stamen color*.—Near White N155B.
- *Anther length*.—Approximately 1.5 cm.
- *Anther color*.—Near RHS Yellow-White 158B.
- *Anther shape*.—Oblong.
- *Pollen quantity*.—Moderate.
- *Pollen color*.—Near White N155C.

Pistil:

- *Length*.—Approximately 0.8 cm.
- *Style length*.—Approximately 0.6 to 0.8 cm.
- *Style color*.—Near RHS Red-Purple 71D.
- *Stigma*.—Shape: Linear. Color: Near RHS Purple 77B.

OTHER CHARACTERISTICS

Seeds and fruits: Not observed to date.

Disease/pest resistance: Neither resistance nor susceptibility to normal pests of *Clematis* has been observed. Better resistance for mildew diseases of *Clematis* has been observed. The most common known mildew pathogen is *Erysiphe aquilegiae*.

Temperature tolerance: Tolerates temperatures from approximately −25° C. to 45° C.

What is claimed is:

1. A new and distinct cultivar of *Clematis* hybrid plant named 'KBK06' as herein illustrated and described.

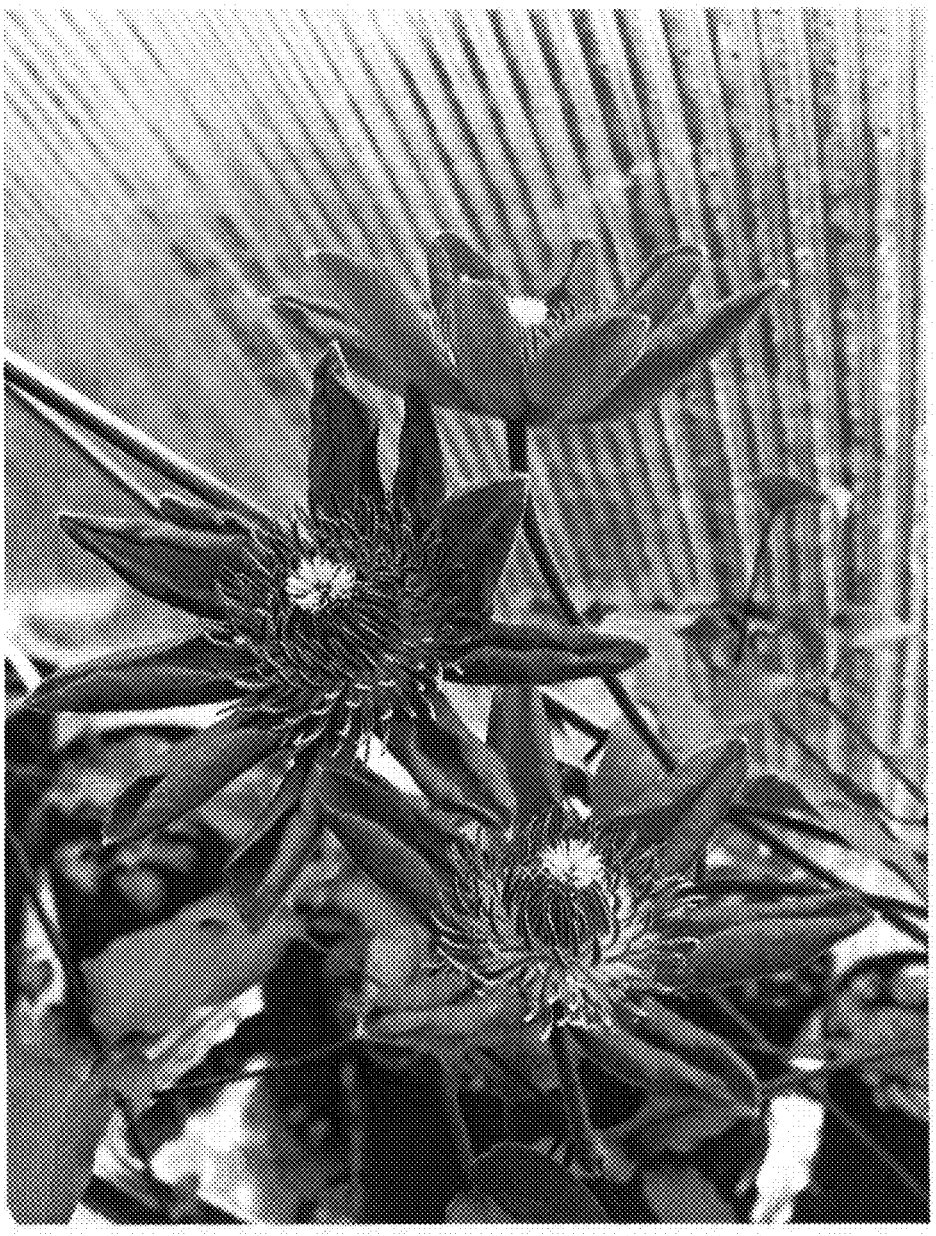

* * * * *